(12) United States Patent
Vetter et al.

(10) Patent No.: US 6,241,667 B1
(45) Date of Patent: Jun. 5, 2001

(54) CATHETER APPARATUS FOR GUIDED TRANSVASCULAR TREATMENT OF ARTERIAL OCCLUSIONS

(75) Inventors: James W. Vetter; Tomoaki Hinohara, both of Portola Valley; Matthew R. Selmon, Woodside; Charles F. Milo, Union City, all of CA (US)

(73) Assignee: LuMend, Inc., Redwood City, CA (US)

( * ) Notice: Subject to any disclaimer, the term of this patent is extended or adjusted under 35 U.S.C. 154(b) by 0 days.

(21) Appl. No.: 09/008,198

(22) Filed: Jan. 15, 1998

Related U.S. Application Data (63) Continuation-in-part of application No. 09/007,434, filed on Jan. 15, 1998, now Pat. No. 6,081,738.

(51) Int. Cl.[7] .................................................. A61B 17/00
(52) U.S. Cl. ........................... 600/407; 606/189; 606/198
(58) Field of Search .................................... 600/427, 424, 600/433–435, 407; 606/151–156, 189, 198; 128/898; 604/96, 104, 164; 623/1, 2

(56) References Cited

U.S. PATENT DOCUMENTS

| 3,640,270 | 2/1972 | Hoffmann | 128/2.1 E |
|---|---|---|---|
| 4,355,643 | 10/1982 | Laughlin et al. | 128/632 |
| 4,447,227 | 5/1984 | Kotanis | 604/95 |

(List continued on next page.)

FOREIGN PATENT DOCUMENTS

| 2945237 A1 | 5/1981 | (DE) | A61B/17/22 |
|---|---|---|---|
| 4429117 A1 | 2/1996 | (DE) | A61M/29/00 |
| 0 117 519 A1 | 5/1984 | (EP) | A61B/17/22 |
| 0 245 211 A1 | 11/1987 | (EP) | A61M/25/00 |
| 0 377 269 A1 | 7/1990 | (EP) | A61M/25/01 |
| 1585065 | 1/1970 | (FR) . | |
| WO83/03188 | 9/1983 | (WO) | A61B/1/06 |
| WO91/19528 | 12/1991 | (WO) | A61M/29/00 |
| WO92/08510 | 5/1992 | (WO) | A61M/25/00 |
| WO93/18818 | 9/1993 | (WO) | A61M/37/00 |
| WO 93/20882 | 10/1993 | (WO) | A61M/29/02 |
| WO95/19143 | 7/1995 | (WO) | A61B/17/22 |
| WO96/01590 | 1/1996 | (WO) | A61B/17/22 |
| PCT/US96/16268 | 4/1997 | (WO) | A61B/19/00 |
| PCT/US96/16483 | 4/1997 | (WO) | A61B/17/00 |
| WO 97/13463 | 4/1997 | (WO) | A61B/17/00 |

(List continued on next page.)

*Primary Examiner*—Marvin M. Lateef
*Assistant Examiner*—Eleni Mantis Mercader
(74) *Attorney, Agent, or Firm*—Wilson Sonsini Goodrich and Rosati (57) ABSTRACT

An apparatus is described for treating arterial occlusions combining an intraluminally operable catheter having an occlusion-crossing working element, with an extraluminally operable locator for imaging the progress of the working element through the occlusion. Suction coupling means are described for removably anchoring the locator to a surface proximate the heart. A method for treating arterial occlusions is described in which the distal end of the catheter shaft exits a lumen of the locator, penetrates the arterial wall distal to the occlusion, crosses the occlusion retrograde and passes into a separately introduced standard intravascular catheter, whereupon the distal end of the shaft may be manipulated from the proximal end of the standard catheter. The proximal end of the shaft is then released from external attachments and drawn into the artery to perform treatment or guiding functions. Spatial interrelationships are observed real-time via the locator. Conical, abrasive, blunt-dissecting, sharp-pointed and guide-wire type working elements, steerable and non-steering, are described. Acoustic transducers and a flexible imaging tube are described for the locator. A signal-emitting working element and cooperating signal-receiving locator are described.

35 Claims, 7 Drawing Sheets

U.S. PATENT DOCUMENTS

| | | | |
|---|---|---|---|
| 4,541,433 | 9/1985 | Baudino | 128/668 |
| 4,631,052 | 12/1986 | Kensey | 604/22 |
| 4,648,402 | 3/1987 | Santos | 128/345 |
| 4,698,057 | 10/1987 | Joishy | 604/176 |
| 5,000,185 | 3/1991 | Yock | 128/662.03 |
| 5,001,556 | 3/1991 | Nakamura et al. | 358/98 |
| 5,019,040 | 5/1991 | Itaoka et al. | 604/95 |
| 5,085,221 | 2/1992 | Ingebrigsten et al. | 128/660.1 |
| 5,099,850 | 3/1992 | Matsui et al. | 128/662.06 |
| 5,102,390 | 4/1992 | Crittenden et al. | 604/96 |
| 5,114,414 | 5/1992 | Buchbinder | 604/95 |
| 5,158,564 | 10/1992 | Schnepp-Pesch et al. | 606/159 |
| 5,181,514 | 1/1993 | Solomon et al. | 128/660.09 |
| 5,193,546 | 3/1993 | Shaknovich | 128/622.06 |
| 5,247,938 | 9/1993 | Silverstein et al. | 128/662.03 |
| 5,256,141 | 10/1993 | Gencheff et al. | 604/53 |
| 5,279,565 | 1/1994 | Klein et al. | 604/105 |
| 5,306,244 | 4/1994 | Shiber | 604/53 |
| 5,321,501 | 6/1994 | Swanson et al. | 356/345 |
| 5,325,845 | 7/1994 | Adair | 128/4 |
| 5,325,860 | 7/1994 | Seward et al. | 128/662.06 |
| 5,336,252 | 8/1994 | Cohen | 607/119 |
| 5,350,377 | 9/1994 | Winston et al. | 606/15 |
| 5,383,467 | 1/1995 | Auer et al. | |
| 5,397,301 | 3/1995 | Pflueger et al. | 604/22 |
| 5,409,453 | 4/1995 | Lundquist et al. | 604/22 |
| 5,419,767 | 5/1995 | Eggers et al. | 604/114 |
| 5,423,846 | 6/1995 | Fischell | 606/180 |
| 5,425,705 | 6/1995 | Evard et al. | 604/28 |
| 5,439,000 | 8/1995 | Gunderson et al. | 128/664 |
| 5,452,733 | 9/1995 | Sterman et al. | 128/898 |
| 5,459,570 | 10/1995 | Swanson et al. | 356/345 |
| 5,474,065 | 12/1995 | Meathrel et al. | 128/640 |
| 5,484,412 | 1/1996 | Pierpont | 604/101 |
| 5,486,170 | 1/1996 | Winston et al. | 606/16 |
| 5,501,698 | 3/1996 | Roth et al. | 606/205 |
| 5,507,295 | 4/1996 | Skidmore | 128/662.06 |
| 5,507,795 | 4/1996 | Chiang et al. | 606/167 |
| 5,531,677 | 7/1996 | Lundquist et al. | 604/22 |
| 5,549,542 | 8/1996 | Kovalcheck | 600/146 |
| 5,569,276 | 10/1996 | Jang et al. | 606/159 |
| 5,571,215 | 11/1996 | Sterman et al. | 623/66 |
| 5,573,531 | 11/1996 | Gregory | 606/14 |
| 5,607,421 | 3/1997 | Jeevanandam et al. | 606/15 |
| 5,651,378 | 7/1997 | Matheny et al. | 128/989 |
| 5,702,368 | 12/1997 | Stevens et al. | 604/171 |
| 5,704,898 | 1/1998 | Kokish | 600/141 |
| 5,709,693 | 1/1998 | Taylor | 606/145 |
| 5,807,388 | 9/1998 | Jeevanandam et al. | 606/15 |
| 5,830,222 | 11/1998 | Makower | 606/159 |
| 5,836,882 | 11/1998 | Frazin | 600/462 |
| 5,868,760 | 2/1999 | McGuckin, Jr. | 606/139 |
| 5,876,373 | 3/1999 | Giba et al. | 604/95 |
| 5,885,238 | 3/1999 | Stevens et al. | 604/4 |
| 5,968,064 | 10/1999 | Selmon et al. | 606/189 |

FOREIGN PATENT DOCUMENTS

| | | | |
|---|---|---|---|
| WO 97/27897 | 7/1997 | (WO) | A61M/29/00 |
| PCT/US97/01459 | 8/1997 | (WO) | A61M/29/00 |
| PCT/US97/01463 | 8/1997 | (WO) | A61M/19/00 |
| PCT/US97/01468 | 8/1997 | (WO) | A61M/29/00 |
| WO98/08456 | 3/1998 | (WO) | A61B/19/00 |
| WO98/16161 | 4/1998 | (WO) | A61B/17/36 |

CATHETER APPARATUS FOR GUIDED TRANSVASCULAR TREATMENT OF ARTERIAL OCCLUSIONS

This application is a continuation-in-part application of U.S. patent applicaton Ser. No. 09/007,434 filed Jan. 15, 1998, currently issued as U.S. Pat. No. 6,081,738 and is related to U.S. patent application Ser. No. 09/008,033 and issued on Mar. 23, 2000.

BACKGROUND OF THE INVENTION

1. Field of the Invention

This invention relates generally to catheters and more particularly to catheter apparatus for treating severe or total arterial occlusions. The invention relates especially to the combination of an extravascularly operable imaging and therapeutic device and an intravascular catheter shaft.

2. Background

Atherosclerosis is a disease in which the lumen (interior passage) of an artery becomes stenosed (narrowed) or even totally occluded (blocked) by an accumulation of fibrous, fatty, or calcified tissue. Over time this tissue, known in medicine as an atheroma, hardens and occludes the artery. In the coronary arteries, which supply the heart muscle, this process leads to ischemia (deficient blood flow) of the heart muscle, angina (chest pain), and, eventually, infarction (heart attack) and death. Although drug therapies and modifications to diet and lifestyle show great promise for preventing and treating atherosclerotic vascular disease, many patients urgently require restoration of blood flow that has already been lost, especially in those having severely or totally occluded blood vessels. Unfortunately, the demand for surgical treatment of disabling and life-threatening coronary artery disease will likely increase in the decades ahead.

It has been common surgical practice to treat severe coronary artery disease by performing a coronary bypass, in which a segment of the patient's saphenous vein (taken from the leg) is grafted onto the artery at points upstream and downstream of the stenosis. The bypass often provides dramatic relief. However, this procedure involves not only dangerous open chest surgery, but also an operation on the patient's leg to obtain the segment of saphenous vein that is used for the bypass. Additionally, there is a long, often complicated and painful, convalescence before the patient is healed. Moreover, within a few years, the underlying disease may invade the bypass graft as well. The bypass can be repeated, but at ever greater peril and expense to the patient.

Fortunately, for patients with moderate stenosis, a less traumatic operation is available. A typical mechanical device for such operations is a thin, flexible, tubular device called a catheter. Through a small, conveniently located puncture, the catheter is introduced into a major artery, typically a femoral artery. Under fluoroscopic observation, the catheter is advanced and steered through the arterial system until it enters the stenosed region. At the distal (tip) end of the catheter, a balloon, cutter, or other device dilates the stenosed lumen or removes atheromatous tissue.

Cardiac catheterization procedures for treating stenoses include percutaneous transluminal coronary angioplasty (PTCA), directional coronary atherectomy (DCA), and stenting. PTCA employs a balloon to dilate the stenosis. A steerable guide wire is inserted into and through the stenosis. Next, a balloon-tipped angioplasty catheter is advanced over the guide wire to the stenosis. The balloon is inflated, separating or fracturing the atheroma. Ideally, the lumen will remain patent for a long time. Sometimes, however, it will restenose.

In directional coronary atherectomy, a catheter, containing a cutter housed in its distal end, is advanced over the guide wire into the stenosis. The housing is urged against the atheroma by the inflation of a balloon. Part of the atheroma intrudes through a window in the housing and is shaved away by the cutter.

Stenting is a procedure in which a wire or tubular framework, known as a stent, is compressed onto a balloon catheter and advanced over the guidewire to the stenosis. The balloon is inflated, expanding the stent. Ideally, the stent will hold the arterial lumen open for a prolonged period during which the lumen will remodel itself to a healthy, smooth configuration. Stents are often placed immediately following PTCA or DCA.

It must be noted, however, that a severe stenosis may be untreatable by stenting, DCA, or PTCA. The catheters used in these operations are advanced to their target over a guide wire which has already crossed the stenosis. Most guide wires, however, are too slender and soft-tipped to penetrate the calcified tissue of a severe or total occlusion. Additionally, most guide wires have a bent steering tip which is easily trapped or diverted by the complex, hard tissues often found in a severe stenosis. Without a guidewire to follow, neither PTCA nor DCA nor stenting is feasible and the interventionist may have to refer the patient to bypass surgery. Additionally, degeneration makes a saphenous vein graph a risky and therefore undesirable site of intervention.

Thus, many patients would benefit from a less traumatic alternative to the bypass for restoring circulation after a coronary artery has become severely stenosed or totally occluded. In particular, many such patients would benefit from an operation for crossing the severe or total occlusion without inflicting the gross trauma of classical bypass surgery. In particular, such a procedure is needed for safely forging a path of low mechanical resistance through or around the tough, complex tissues of the severely or totally occlusive atheroma so that blood flow can be restored.

It would be beneficial if a cardiologist could safely cross an occlusion using instruments deliverable by cardiac catheterization or through a small incision in the patient's chest. Instruments have been developed which are deliverable to the site of an occlusion by a cardiac catheter and are capable of penetrating the tissues of a severe or total occlusion or piercing the arterial wall. However, penetrating the arterial wall is what cardiac catheterization procedures usually strive to avoid, because perforation can easily lead to cardiac tamponade. What is needed is a way of reliably selecting the points at which the wall of an artery can be safely penetrated by a catheter working element. What is also needed is a way of reliably guiding the working element from that point of penetration through an occlusion and into another patent portion of the arterial lumen. What is also needed is a way of guiding the working element through interstitial tissue to an appropriately selected point of transvascular entry into an artery.

Likewise, it would be advantageous to reopen the natural lumen of a severely or totally occluded artery so that a stent can be installed or DCA or PTCA can be performed, preferably without straying into the subintimal space or creating a false lumen. Thus, it would be highly advantageous to have a reliable, accurate way of steering and operating a catheter working element along a safe path through the atheromatous tissues of the occlusion.

One guidance system used in coronary catheterization is fluoroscopy, a real-time X-ray technique which is widely used to position devices within the vascular system of a patient. For visualizing a totally occluded artery, biplane fluoroscopy can be used, wherein the interventionist observes two real-time x-ray images acquired from different angles. Biplane fluoroscopy, however, is unreliable, costly and slow.

Another way of imaging the coronary arteries and surrounding tissues is intravascular ultrasound, which employs an ultrasonic transducer in the distal end of a catheter. The catheter may be equipped with an ultraminiature, very high frequency scanning ultrasonic transducer designed to be introduced into the lumen of the diseased artery. Frustratingly, however, the stenosis is often so severe that the transducer will not fit into the part that the interventionist most urgently needs to explore. Indeed, if the occlusion is too severe to be crossed by a guide wire, it may be too difficult to steer the transducer into the segment of greatest interest. Additionally, an attempt to force an imaging catheter into a severely stenosed artery may have undesirable consequences. Alternatively, the intravascular ultrasonic catheter can be placed in a vein adjacent the occluded artery. Because venous lumina are slightly broader than arterial lumina and rarely if ever stenosed, a larger transducer may be employed. Depending on its configuration, a larger transducer may acquire images over greater distances, with finer resolution, or both. However, there is not always a vein properly situated for such imaging.

While superior imaging alone is of diagnostic interest, imaging and guidance for effective intervention for severe occlusive arterial disease is what is truly desired. A reliable imaging technique is needed for discerning precisely the relative positions of a therapeutic working element, the boundaries of the atheromatous tissues of an occlusion, and the structure of the occluded artery as the working element is manipulated.

What is needed is an effective combination of a working element and an imaging system for precisely crossing a severe or total coronary occlusion without causing cardiac tamponade. In particular, such a combination is desired which continuously displays a stable image of the atheroma, the structure of the artery, and the working element as the interventionist maneuvers the working element. What is especially needed is such a combination which is deliverable and operable with minimal trauma to blood vessels and surrounding tissues.

SUMMARY OF THE INVENTION

It is an object of the present invention to treat severe or total arterial occlusions by minimally invasive means and, more particularly, to cross such occlusions without causing cardiac tamponade, so that the circulation to tissues supplied by the occluded artery is increased with minimal invasiveness and low risk to the patient. It is also an object of the present invention to open a path of low mechanical resistance through the atheromatous tissues of the severely occluded artery so that a guide wire, or PTCA catheter, DCA catheter, or stent delivery catheter can be placed across the occlusion.

It is an additional object of the present invention to provide a combination of an effective steerable transvascular working element and a locator device for continuously visualizing the working element and its anatomical environment, so that the working element can be safely directed through the arterial wall and atheromatous tissues as needed to reach and cross the occlusion.

It is an additional object of the present invention to provide a combination of a catheter shaft, including a steerable transvascular working element, and a locator for guiding the working element, the locator including an extravascularly operable imaging device and being positionable proximate the occluded coronary artery through a small incision in the patient's chest and being removably attachable to bodily tissues proximate the artery.

It is an additional object of the present invention to provide a combination of such a catheter shaft and locator in an apparatus which can be inserted into the body through a single incision.

It is an additional object of the present invention to provide such a combination in which the catheter shaft reaches the vascular tissues at a location within the imaging field of the locator.

It is an additional object of the present invention to provide such a combination in which the catheter shaft and the imaging device can be stabilized with respect to the surface of a beating heart while the imaging and operation are accomplished.

It is an additional object of the present invention to treat an artery using such a combination in conjunction with a separate intravascular catheter, which has been introduced in the traditional manner, to control a catheter shaft, guide wire or other such elongate device from either end or both ends.

It is an additional object of the present invention to permit the release of the proximal end of the catheter shaft or guide wire from any external control apparatus, thus allowing what had been the proximal end to be manipulated or positioned within the arterial system.

In accordance with the above objects and those that will be mentioned and will become apparent below, an apparatus for treating arterial occlusions in accordance with the present invention comprises:

a locator including an imaging tube having a proximal end zone, a distal end zone, a lumen therebetween, and an imaging device operatively disposed in the imaging tube;

an elongated flexible catheter shaft, disposed in the lumen of the imaging tube, including a distal end zone and a working element disposed therein, whereby the locator is extraluminally placed proximate the arterial occlusion, the working element is transvascularly operable upon the occlusion, and the locator provides spatial information for effective manipulation of the working element to treat the occlusion.

An exemplary embodiment of the catheter apparatus according to the present invention includes a steering member including a plurality of steering wires disposed in the catheter shaft. The steering wires are fixed in the distal end zone of the catheter shaft, optionally attached to a retaining ring therein and, also optionally, confined in tubes for preventing mechanical interference, and are manipulable from the proximal end of the catheter shaft. The steering wires provide the apparatus of the present invention with the ability to steer the distal end of the catheter shaft, and thus the working element, by applying unequal tension to different steering wires.

Another exemplary embodiment of the catheter apparatus according to the present invention includes a plurality of rigid tubes confining the steering wires. The rigid tubes have distal ends some distance proximal to the distal ends of the steering wires, thereby increasing the flexibility of the intervening segment of the distal end zone of the catheter shaft.

Another exemplary embodiment of the catheter apparatus according to the present invention includes a working element including a pointed tissue-penetrating wire for crossing an occlusion and for penetrating the arterial wall to reach the occlusion. This provides the apparatus of the present invention with the ability to precisely select the point of entry of the working element into the vascular or atheromatous tissue that is to be penetrated.

Another exemplary embodiment of the catheter apparatus according to the present invention includes a working element including a plurality of slots partially circumscribing the distal end zone of the catheter shaft. This provides the apparatus of the present invention with the ability to deflect the distal end of the catheter shaft with only a gentle force supplied by the steering member, while preserving the axial incompressibility of the catheter shaft and so its suitability for pushing the distal end against and through an occlusion or other tissue.

Another exemplary embodiment of the catheter apparatus according to the present invention includes a working element (for example, a guide wire or other tissue penetrating or treatment device) which emits a signal, and a locator which detects the signal emitted by the working element, whereby a spatial relationship between the working element and the locator is discernible. This provides the apparatus of the present invention with the ability to readily locate the working element.

Another exemplary embodiment of the catheter apparatus according to the present invention includes an extravascularly operable imaging tube having a distal end zone defining a surface including a suction coupling area for adhesion to a beating heart. This provides the apparatus of the present invention with the ability to stabilize the imaging device with respect to the blood vessels and occlusion.

Another exemplary embodiment of the catheter apparatus according to the present invention includes an extravascularly operable imaging tube having a distal end zone. A surface of the distal end zone defines an acoustic window. A catheter delivery lumen terminates in an orifice proximate the acoustic window. This provides the apparatus of the present invention with the ability to view an image of the catheter shaft or guide wire as it emerges from the orifice and as it is advanced through the occlusion or arterial wall.

Another exemplary embodiment of the catheter apparatus according to the present invention includes an extravascularly operable imaging tube having a distal end zone having a surface defining an imaging window and a plurality of suction coupling areas disposed peripherally about the window for adhesion to a beating heart. A catheter delivery lumen terminates in an orifice proximate the window. This provides the apparatus of the present invention with the ability to stabilize the imaging device and the catheter shaft with respect to the vessels and the occlusion while viewing an image of both and manipulating the catheter shaft and working element. The multiple peripherally arranged suction coupling areas provide enhanced stabilization without obstructing the imaging device or catheter shaft.

Another exemplary embodiment of the catheter apparatus according to the present invention includes an acoustic transducer affixed to a transducer control shaft disposed in a lumen of the imaging tube. The control shaft is mechanically manipulable by external control apparatus. The transducer is operatively coupled to external signal generating and processing apparatus for displaying an image. This provides the apparatus of the present invention with the ability to display a scanning ultrasound image of the catheter shaft, working element, occlusion, and surrounding vascular and interstitial tissues as the operation is performed.

Another exemplary embodiment of the catheter apparatus according to the present invention includes an array of acoustic transducers disposed in the imaging tube and operatively coupled to external signal generating and processing apparatus for displaying an image. This provides the apparatus of the present invention with the ability to display an ultrasound image of the catheter shaft, working element, occlusion and surrounding vascular and interstitial tissues as the operation is performed without necessarily employing a rotating or translating transducer control shaft. More generally, this provides an expanded imaging field, enhanced image resolution, or both, with reduced need for moving parts.

Also in accordance with the above objects and those that will be mentioned and will become apparent below, method for treating an arterial occlusion having a distal boundary and a proximal boundary in a human or animal body in accordance with the present invention comprises the steps of:

providing a apparatus for treating an arterial occlusion, the apparatus comprising:

a locator including an imaging tube including a proximal end zone, a distal end zone, a lumen therebetween, and an imaging device operatively disposed in the imaging tube; and an elongated flexible catheter shaft, disposed in the lumen of the imaging tube, including a distal end zone and a working element disposed therein;

introducing the locator into the patient's chest, placing the distal end zone of the locator proximate the distal boundary of the occlusion, and activating the locator to discern the anatomical location and position of the working element;

while observing the anatomical location and position of the working element via the locator, advancing the catheter shaft into contact with the artery;

while continuing the observation, advancing the working element through an arterial wall and into the artery; and while continuing the observation, advancing the working element retrograde within the artery and into and through the occlusion until the working element exits the occlusion via the proximal boundary of the occlusion;

whereby the locator, catheter shaft and working element are positioned proximate the occlusion and the working element is operated to cross the occlusion, while the locator reveals the anatomical location and orientation of the working element to accomplish the effective manipulation of the working element.

In an exemplary method according to the present invention, the working element is steerable and is steered within the artery under observation via the locator.

In another exemplary method according to the present invention, the working element, which may be, for example, a steerable catheter, a simple catheter, or a guide wire, is passed retrograde, through the occlusion, into a lumen of a separate intravascular catheter which has been placed in the arterial lumen proximal to the occlusion via femoral arteriotomy. The distal end of the catheter shaft or guide wire is passed through the separate intravascular catheter to the proximal end thereof and coupled to external control apparatus, such that both ends may be simultaneously externally controlled.

In another exemplary method according to the present invention, the proximal end of the catheter shaft or guide wire is then released from its attachments and drawn into the artery to perform a therapeutic or guiding function while being controlled from the distal end.

An advantage of the present invention is that the working element and the distal end of the catheter shaft can be steered, the catheter shaft pushed, pulled or twisted, and the working element operated according to its particular design, all while the effect of these actions is immediately and continuously observable via the locator.

An additional advantage of the present invention is that the catheter shaft may be provided with a highly flexible distal end zone for precise maneuvering to exploit high resolution imaging available from the extravascularly operable locator.

An additional advantage of the present invention is that it permits the use of cardiac catheterization techniques for restoring blood flow to severely or totally occluded coronary arteries previously inaccessible to those techniques. A related advantage is that patients can enjoy relief from cardiac ischemia while avoiding the trauma of coronary bypass surgery. Another related advantage is that the native artery can be preserved and, with it, the artery's superior blood-carrying characteristics and ability to withstand repeated surgical intervention.

An additional advantage of the present invention is the ability to guide a working element through the tissues of a severe or total occlusion, and into the artery through the artery wall to reach the occlusion, without causing uncontrolled hemorrhage or tamponade. A related advantage is the ability to provide safe access for a guide wire or other catheter to cross a severe or total occlusion.

An additional advantage of the present invention is the provision of a stable, real-time image of the vasculature, the disease and the working element that is being guided therein, allowing accurate determination of the spatial relationships of the working element, the boundaries of the occlusion, and the structures of the artery and interstitial tissues. Thus, the working element can safely and accurately penetrate the occlusion.

An additional advantage of the present invention is the effective micro-invasive placement of the locating device in the vicinity of the occlusion, requiring only a small, minimally traumatic incision in the patients chest.

An additional advantage of the present invention is the provision of a scanning ultrasound image of the catheter shaft and its anatomical environment from an imaging device which is stabilized on the surface of a beating heart. Thus, it is easier to visualize important spatial relationships while manipulating the catheter shaft and working element.

An additional advantage of the present invention is the provision of a catheter shaft which is viewable via the imaging device immediately upon its emergence from the orifice in the imaging tube, so that it is always possible to know what tissues the working element is in contact with and what tissues lie ahead.

An additional advantage of the present invention is the simultaneous stabilization of both the imaging device and the catheter shaft with respect to the surface of the beating heart, so that conditions are optimized for precise placement of the working element through tissues.

An additional advantage of the present invention is the ability to simultaneously control both ends of a catheter shaft or guide wire which is placed in an artery.

An additional advantage of the present invention is the ability to introduce a catheter shaft or guide wire into an artery trans-luminally, pass the distal end of the catheter shaft or guide wire retrograde to a separate point of access to the arterial system, and either directly control both ends of the catheter shaft or guide wire simultaneously, or detach the proximal end and draw the free proximal end into the artery by directly manipulating the distal end.

BRIEF DESCRIPTION OF THE DRAWINGS

For a further understanding of the objects and advantages of the present invention, reference should be had to the following detailed description, taken in conjunction with the accompanying drawings, in which like parts are given like reference numerals and wherein.

DETAILED DESCRIPTION OF THE INVENTION

Figure 1:
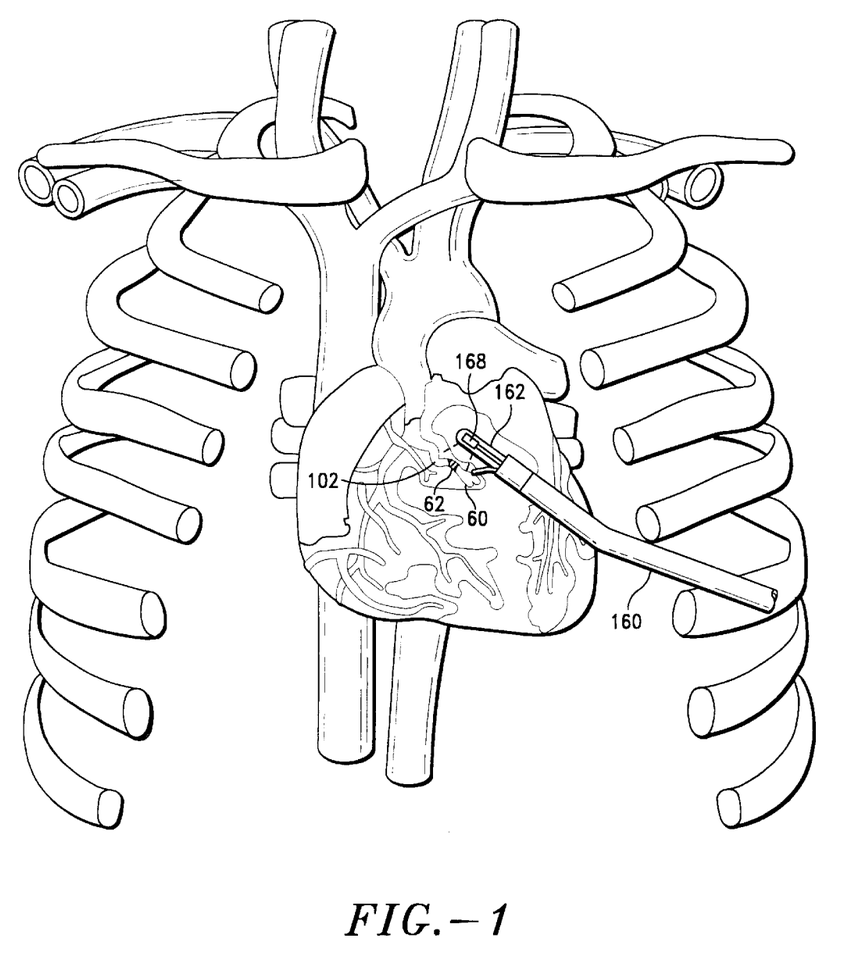
FIG. 1 illustrates an exemplary embodiment of the apparatus in accordance with this invention placed in a human chest cavity proximate a coronary artery having an occlusion.
Figure 2:
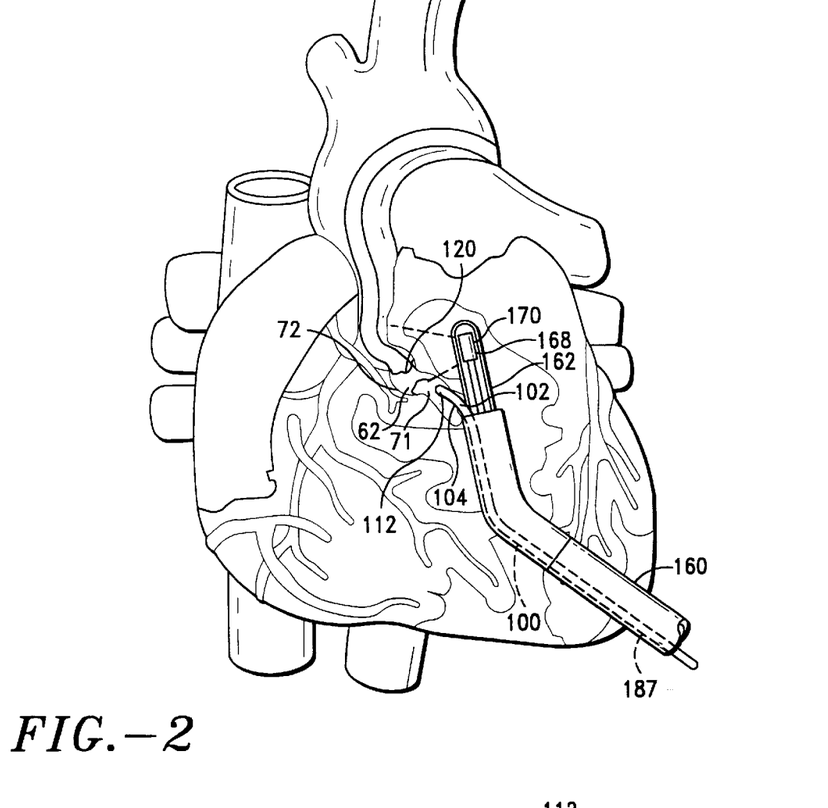
FIG. 2 is an enlarged view of the exemplary embodiment of FIG. 1 placed proximate the occlusion.

The invention is now described particularly with reference to a coronary artery having an occlusion. As illustrated in FIGS. 1 and 2, an exemplary embodiment of the catheter apparatus in accordance with the present invention is shown placed proximate the occlusion 62 in the coronary artery 60. The apparatus of the present invention embodies a combination of two devices which cooperate to safely bypass the occlusion 62. The first device is an imaging locator 160 including an imaging tube 162 and an imaging device 168. The imaging tube 162 is introduced through a small incision (not shown) in the patient's chest and positioned adjacent the heart and proximate the occlusion 62. The imaging tube 162 includes a catheter (or guide wire) delivery lumen (not shown). The second device is a catheter shaft 100 including a distal end zone 104 and a steerable tissue-penetrating working element 102. The catheter shaft 100 is disposed in the catheter delivery lumen (not shown) of the imaging tube 162. During the operation, the catheter shaft 100 and work element 102 are advanced from the catheter delivery lumen and steered and manipulated through the patient's tissues while being imaged by the locator 160.

Continuing with reference to FIG. 1 and now also to FIG. 2, the imaging tube 162 is introduced through an incision large enough to slip the imaging tube 162 into the patient's chest. The imaging tube is introduced, for example, by thoracotomy, thoracoscopy or sub-xyphoid access, is passed through a puncture in the pericardium, and is advanced until it is adjacent the surface of the heart. The external imaging instruments (not shown) are then activated to display an ultrasound image.

Referring to FIG. 2, the two devices are operated simultaneously to safely guide and steer the working element 102 of the catheter shaft 100. The locator 160 is stabilized adjacent the heart and activated to provide an image of the occlusion 62 from a vantage point close to the occluded artery 60 but outside the arterial lumen 71. The catheter shaft 100 emerges from the lumen 187 of the imaging tube 162. It will be appreciated that because only a small puncture or incision is needed in order for the imaging tube 162 to place the imaging device 168 and catheter shaft 100 at the heart surface, the patient can expect a comfortable, uncomplicated recovery. With the present invention there is no need to saw through the patient's sternum or rib cage.

Figure 3:
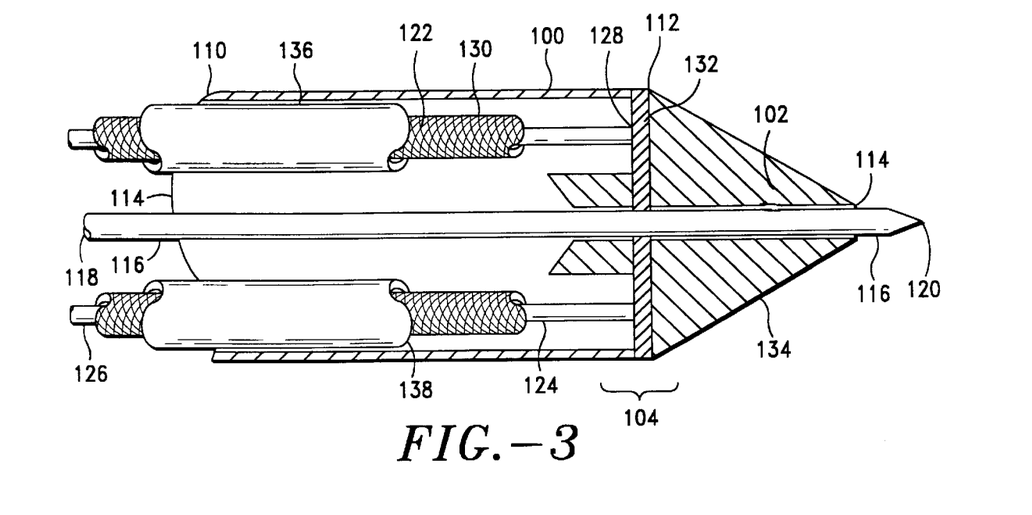
FIG. 3 is an enlarged side view of an exemplary embodiment of an apparatus according to the present invention showing a catheter shaft.

Referring now to FIGS. 2 and 3, the catheter shaft 100 and locator 160 are positionable with minimal trauma in the proximity of the occlusion 62 and are simultaneously operable to direct the working element 102 through the arterial wall 72, into the artery 60, and through the occlusion 62. The elongated flexible catheter shaft 100 (greatly shortened in FIG. 3) includes a steerable distal end zone 104 and a working element 102 which is carried into the proximity of the occlusion by the distal end zone 104. The proximal end zone 106 of the catheter shaft 100 is connectable to external apparatus (not shown) for manipulating the catheter shaft 100 and working element 102. The locator 160 includes an imaging tube 162 for micro-invasive extravascular placement of the imaging device 168 proximate the occluded artery 60. The imaging tube 162 includes a proximal end zone 164 connectable to external imaging instruments (not shown). The locator 160 also includes an imaging device 168 which is locatable extraluminally near the occlusion 62 and is operatively coupled to the external imaging instruments.

Referring now to FIG. 3, the catheter shaft 100 includes a proximal end 110 connectable to external apparatus (not shown), a distal end zone 104 including a distal end 112, and at least one lumen 114 therebetween. A working element 102 for penetrating tissues is disposed in the distal end zone 104. A steering member 122 is disposed in the distal end zone 104 for directing the working element 102 at and through tissues.

Continuing with respect to FIG. 3, the steering member 122 includes a plurality of steering wires 124 slidably disposed in the catheter shaft 100. The steering wires 124 have proximal ends 126 manipulable from the proximal end 110 of the catheter shaft 100 and distal ends 128 fixed in the distal end zone 104 of the catheter shaft 100. Optionally, isolating tubes 130 slidably confine the wires 124 to prevent the wires 124 from interfering with other parts of the catheter shaft 100. Also optionally, the steering wires 124 may be affixed to a retaining ring 132 disposed in the distal end zone 104 of the catheter shaft 100. Also optionally, rigid tubes 136 may be disposed about isolating tubes 130, the rigid tubes 136 having distal ends 138 some distance proximal to the distal ends 128 of the steering wires 124. Between the distal ends 138 of the rigid tubes 136 and the distal end 112 of the catheter shaft 100, the absence of the rigid tubes 136 increases the flexibility of the distal end zone 104 to facilitate steering.

As can be seen from FIG. 3, unequal tension on the steering wires 124 will deflect the distal end zone 104 of the catheter shaft 100 toward a wire 124 having greater tension. It can also be appreciated that, for example, the distal ends 128 of four steering wires 124 may be fixed in the distal end zone 104 of the catheter shaft 100 at ninety degree intervals about the longitudinal axis of the catheter shaft 100, with the result that the distal end 112 of the catheter shaft 100 can be deflected in two dimensions somewhat independently by manipulating the steering wires 124 in combination.

Continuing still with reference to FIG. 3, the working element 102 is steered by deflecting the distal end zone 104 of the catheter shaft 100. Because the working element 102 is carried in the distal end zone 104, the distal end zone 104 will impart to the working element 102 the deflection imparted to the distal end zone 104 by the steering member 122. In conjunction with the guidance provided by the locator 160 (discussed in detail below), this deflection enables an operator of the present invention to guide the working element 102 along a chosen path through the occlusion 62.

Although the embodiment described includes the steering member, a catheter or working element without a discrete steering member and a catheter or working element without a steering function are also within the scope and spirit of the present invention. For example, the apparatus may include a guide wire and the guide wire may include a deflected distal end which functions to steer the guide wire. Likewise, the introduction of a working element into a vascular system and the operation thereof to treat an occlusion without the specific step of steering the working element during treatment is also within the scope and spirit of the method according to the present invention.

The present invention can incorporate a wide variety of working elements. For example, a blunt-dissecting working element of the kind described in copending U.S. patent application No. 08/775,264, filed Feb. 28, 1997, the entire disclosure of which is incorporated herein by reference, may be used.

Continuing with reference to FIG. 3, an exemplary embodiment of the present invention is shown in which the working element 104 includes a tissue-penetrating wire 116 disposed in a lumen 114 of the catheter shaft 100. The tissue-penetrating wire 116 includes a proximal end 118, manipulable through the proximal end 110 of the catheter shaft 100, and a sharp distal end 120 projectable from the distal end 112 of the catheter shaft 100. The tissue-penetrating wire 116 may, for example, be disposed in the lumen 114 of the catheter shaft 100 much as a trocar is disposed in a cannula. Under guidance provided by the locator 160 (discussed below), pressure is applied to the proximal end of the tissue-penetrating wire 116, urging the wire 116 into and through tissues as the catheter shaft 100 and steering member 122 are manipulated to direct the wire 116.

Figure 4:
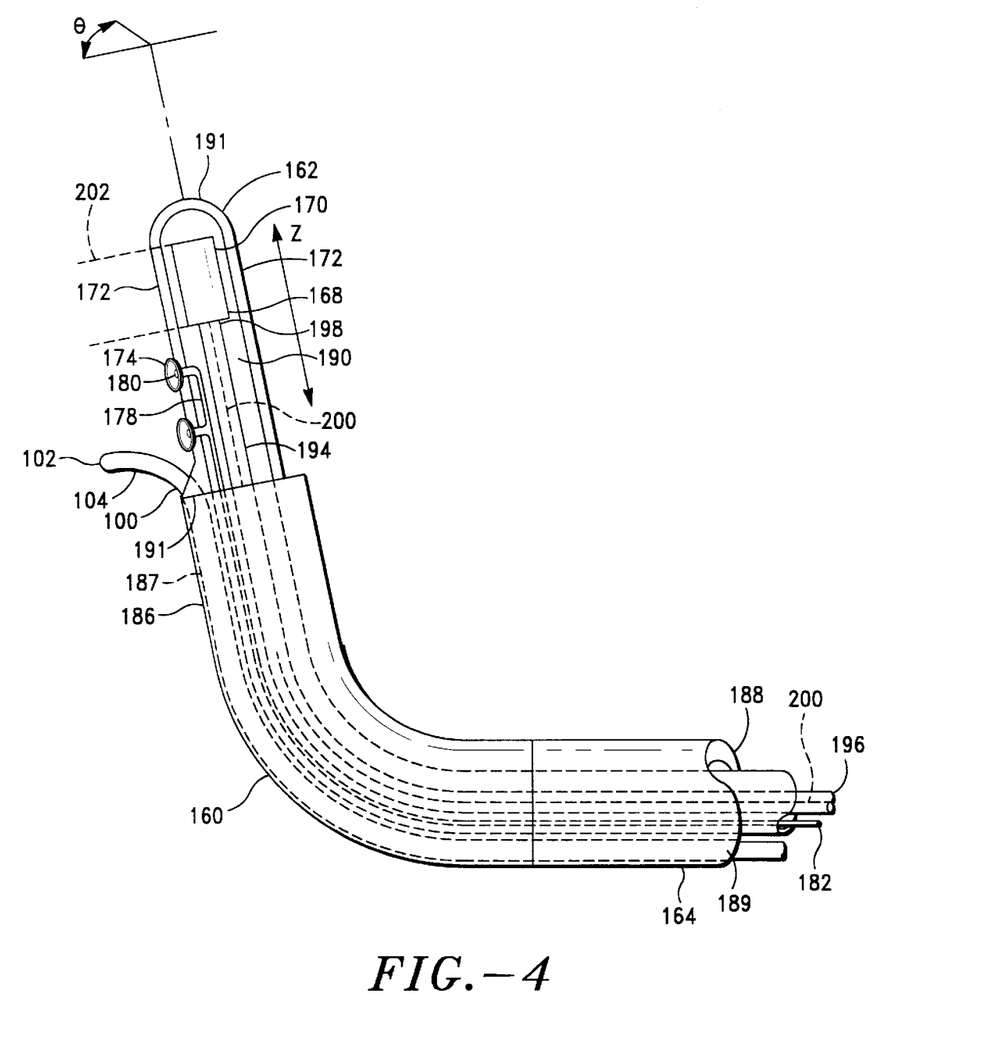
FIG. 4 is an enlarged side view of an exemplary embodiment of an apparatus according to the present invention showing a locator and a catheter shaft disposed in a lumen of the locator.

Referring again to FIG. 2 and now also to FIG. 4, the locator 160 includes an imaging device 168 (in this embodiment, an acoustic transducer 170), an imaging tube 162 for placing the imaging device 168 extraluminally proximate the occlusion, and one or more external imaging instruments (not shown) operatively coupled to the imaging device 168 for discerning the spatial interrelationships of the working element 102, occlusion 62, arterial lumen 71, and arterial wall 72. Optionally, the imaging tube 162 has an exterior surface 172 which forms one or more suction cups 174 for stabilizing the imaging tube 162 on tissues near the artery 60 having the occlusion 62. Also optionally, the imaging tube 162 has a suction cup activator 176 for selectively activating the suction cup 174. As illustrated in FIG. 4, the activator 176 includes a lumen 178 having a distal end 180 communicating with a suction cup 174 and a proximal end 182 communicating with a pressure-modulating device (not shown). The activator 176 may, however, encompass an aspirator, a mechanical means of activating the suction cup 174, or any other convenient way of establishing and interrupting a vacuum to temporarily stabilize a surface of the imaging tube 162 upon a surface proximate the artery 60 and occlusion 62. Generally, the suction cup may take the form of any other suction-coupling area or feature, defined by a surface 172 of the imaging tube 162, which affords adhesion to a surface.

Continuing with reference to FIG. 4, it will be appreciated that the imaging tube 162 can be made flexible, enabling the distal end zone 186 of the imaging tube 162 to be secured adjacent a beating heart while the proximal end zone 164 of the imaging tube 162 remains connected to external instruments (not shown) for support and control. This flexibility of the imaging tube 162 contributes to its micro-invasive quality by reducing the trauma inflicted upon tissues and by permitting the tube 162 to conform to the natural contours of bodily surfaces. As alternative ways of reducing trauma and increasing the ease of use, the imaging tube 162 may be given a shape well suited to the route of entry into the chest, or may be stabilized or flexibly supported by external apparatus at its proximal end 188.

Continuing still with reference to FIG. 4, the imaging tube 162 includes a catheter delivery lumen 187 including a proximal 189 in the proximal end zone 164 of the imaging tube 162 and a distal end 191 in the distal end zone 186 of the imaging tube 162. The catheter shaft 100 is slidably disposed in the lumen 187 so that, after the imaging tube 162 is stabilized on the heart surface, the catheter shaft 100 can be advanced from the lumen 187 into the appropriate bodily tissues while a stabilized image of the catheter shaft 100 and its anatomical environment is displayed via the locator 160.

Continuing still with reference to FIG. 4, the imaging tube 162 includes a proximal end 188, a lumen 190 originating in the proximal end 188, and a motor assembly (not shown) proximate the proximal end 188. A transducer control shaft 194, rotatably and translatably disposed in the lumen 190, includes a proximal end 196 coupled to the motor assembly (not shown), a distal end 198 coupled to the transducer 170, and a signal conducting path 200 operatively coupling the transducer 170 to the external imaging instruments (not shown). The transducer control shaft 194 is flexible enough to match the flexibility of the imaging tube 162. In this embodiment, the external imaging instruments (not shown) include an acoustic signal generator-processor (not shown) and video display device controlled by a suitably programmed general purpose computer.

Continuing still with reference to FIG. 4, the locator 160 in this exemplary embodiment provides a scanning ultrasound image of the environment of the occlusion 62. The imaging tube 162 is stabilized on the heart adjacent the artery 60 containing the occlusion 62. The motor assembly (not shown) drives the transducer control shaft 194 within the lumen 190 of the imaging tube 162 in a scanning pattern appropriate for producing an image. For example, the motor assembly (not shown) may drive the transducer control shaft 194 in a repeating reciprocating patter while at the same time rotating the shaft. In this way, the transducer 170, which is coupled to the transducer control shaft 194, describes a two-dimensional scanning pattern which may be registered by appropriate measuring devices as combinations of a rotational angle θ and a longitudinal position Z within the imaging tube 162.

Continuing still with reference to FIG. 4, as the transducer 170 describes the scanning pattern, the acoustic signal generator-processor (not shown) causes the transducer 170 to emit acoustic energy. A signal conducting path 200 carries a signal (for example, an electrical signal generated or modulated by the transducer or provided for driving the transducer) from the external instruments (not shown) (which include, in this illustration, a signal generator-processor, also not shown) to the transducer 170, which may include a piezoelectric crystal or other device for producing acoustic energy. This acoustic energy is of the type generally referred to as ultrasonic or ultrasound, although these terms may encompass a variety of acoustical signals embodying a variety of frequencies. The energy passes through the surface 172 of the imaging tube 162 and into the occluded artery 60 and surrounding tissues. The transducer 170 and acoustic signal are configured such that the energy is emitted in a narrowly focused beam 202 in a known direction (at a known value of the angle θ) from a known position (at a known value of Z) with respect to the imaging tube 162. The transducer 170 also functions as a similarly directional acoustic signal detector, converting acoustic energy reflected by features in the environment of the imaging tube 162 to a signal which is conducted back to the signal generator-processor and measured accordingly. As are the emitted signals, the detected signals are associated with values of θ and Z.

Continuing still with reference to FIG. 4, a third dimension, which shall be referred to as depth or as radius from the transducer 170 and given the letter r, is computable as a function of the time elapsed between the emission of a given signal by the transducer 170 and the detection of the echo of that signal. The value detected at any given time is a function of the intensity of the echo. With appropriate signal processing, this intensity can be reported via suitable video equipment as a two or three dimensional image of the environment of the imaging tube 162. General purpose computers are programmable to accomplish this function. U.S. Pat. No. 4,794,931, the disclosure of which is incorporated herein by reference in its entirety, describes a computer and instrument system implementing such a function.

Alternatively, a rotating or translating scanning transducer may be supplanted by an array of directional transducers (not shown), a phased array of transducers (not shown) or other appropriately energized and interrogated set of transducers operatively connected to the external signal generator-processor for displaying the desired image.

Referring to FIGS. 2, 3, and 4, the locator 160 provides an image of nearby anatomical features so that the position of the locator 160 with respect to the artery 60 and occlusion 62 is ascertained. The locator 160 is manipulated until its position is ideal for imaging the vessels and tissues to be penetrated. The locator 160 is then stabilized. Optionally, the imaging tube 162 has an exterior surface 172 which including one or more suction cups 174 for stabilizing the imaging tube 162 on tissues near the occluded artery 60. With the locator 160 positioned and functioning, the positions of the distal end 112 of the catheter shaft 100 and the distal end 120 of the working element 102 are ascertained. The contours of the occlusion 62 and the artery 60, as revealed by the locator 160, are also evaluated.

Figure 5:
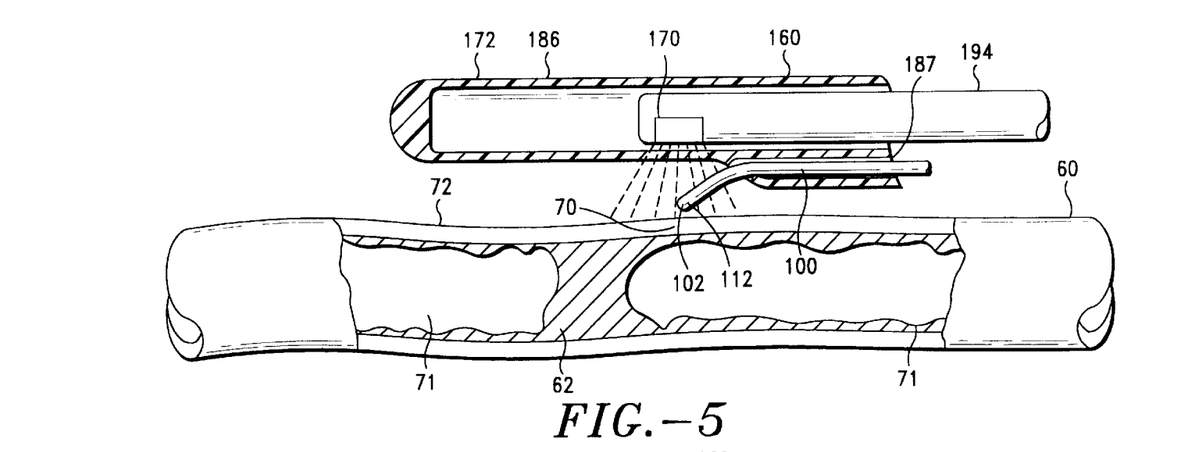
FIG. 5 is a cut-away view of an exemplary embodiment of an apparatus according to the present invention proximate an occluded artery.

Referring back to FIGS. 3 and 4 and now also to FIG. 5, it is seen that the catheter shaft 100 and locator 160 are placed proximate the occlusion 62. The catheter shaft 100 includes a distal end 112, a working element 102, and a proximal end (not shown in FIG. 5). The catheter shaft 100 and steering member 122 are manipulated to direct the working element 102 and the catheter shaft 100 at a point of penetration of the arterial wall 72 for entry into the artery 60. The point of entry 70 will have been identified in the image provided by the locator 160. The image is also studied to determine an appropriate path through or around the atheromatous tissues of the occlusion 62, yet staying within the artery 60.

Although a catheter shaft 100 including a steering member 122 and a tissue penetrating wire 116 is shown in FIG. 3, it should be understood that the catheter delivery lumen 187 may be adapted for the insertion of a catheter of simpler construction, or of a catheter lacking a steering member or discrete work element, or even for the insertion of a guide wire, into the artery. Likewise, a catheter, wire or the like so inserted may be withdrawn and another substituted in its place. Thus, although much of this discussion refers to a catheter shaft as shown in FIG. 3, the invention is not limited to such a catheter shaft and the method of using the invention is not limited to the exact steps in the order described.

Figure 6:
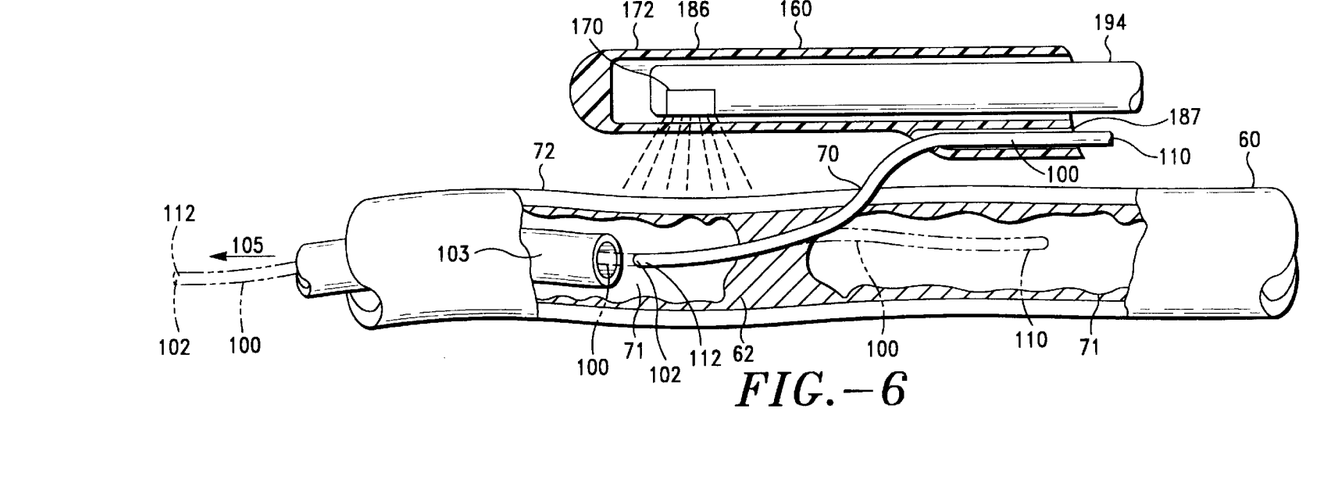
FIG. 6 is a cut-away view of an exemplary embodiment of an apparatus according to the present invention operating transvascularly to cross an arterial occlusion.

Continuing now with reference to FIGS. 3 and 4 and now also to FIG. 6, while control of the working element 102 and catheter shaft 100 is maintained via the steering member, the working element 102 and catheter shaft 100 are urged and steered along the path that has been planned though extravascular tissue, then through the arterial wall 72 into the arterial lumen 71 distal to the occlusion 62, and then in a retrograde direction through the occlusion 62 until the working element 102 is observed to cross the occlusion 62 and re-enter the arterial lumen 71 proximal to the occlusion 62. FIG. 6 illustrates the catheter shaft 100 and working element 102 entering the artery 60 immediately distal to the occlusion 62 and crossing the occlusion 62 in the retrograde direction.

Continuing with particular reference to FIG. 6, a separate intravascular catheter 103 is placed in the lumen 71 of the artery 60 proximal to the occlusion 62. This separate intravascular catheter 103 may be introduced using traditional techniques (for example, via femoral arteriotomy). The separate intravascular catheter 103 has a distal end 107, a proximal end (not shown) and at least one lumen 109 therebetween. The catheter shaft 100 with work element 102 (or catheter shaft, or guide wire, as the case may be) is advanced retrograde into the lumen 109 of the separate intravascular catheter 103 and is then advanced substantially to the proximal end of the separate intravascular catheter 103. At the proximal end of the separate intravascular catheter shaft, the distal end 112 of the catheter shaft 100 is then grasped and controlled by external apparatus (not shown).

The proximal end 110 of the catheter shaft 100 (shown in FIG. 6) is released from any external connections. By moving the distal end 112 of the catheter shaft 100 in the retrograde direction (indicated by arrow 105, toward the femoral arteriotomy), the interventionist draws the free proximal end 110 of the catheter shaft 100 (or guide wire, as the case may be) out of the catheter delivery lumen 187, through the point of entry 70, and into the artery 60 until the proximal end 110 of the catheter shaft 100 is positioned in the lumen 71 of the artery 60 distal to the occlusion 62. In this way, the catheter shaft 100 (or guide wire, as the case may be) is placed across the occlusion 62 and can be used to treat the occlusion 62 or to guide other over-the-wire devices into and through the occlusion 62.

Continuing with reference to FIGS. 5 and 6, as the working element 102 and catheter shaft 100 are advanced along this path, their positions with respect to the arterial anatomy, the occlusion 62 and the separate intravascular catheter 103 are carefully noted from the image provided by the locator 160. The steering member 122 is manipulated to direct the working element 102 away from any contact perceived as likely to cause cardiac tamponade or other unintended trauma. The distal end 112 of the catheter shaft 100 is guided through the occlusion 62 and into the separate intravascular catheter 103.

Referring again to FIG. 2, it is seen that the catheter shaft 100 and the locator 160 of the present invention cooperate to enable the interventionist to guide the working element 102 into and through the occlusion 62 while knowing the anatomical location and orientation of the catheter shaft 100 and maintaining control thereof via the catheter shaft 100 and steering member 122. Thus, the occlusion 62 can be crossed safely and efficiently. Additionally, it is seen that the same cooperation enables the interventionist to pass the catheter shaft (or a guide wire) into a separately introduced intravascular catheter, providing a greater range of options for controlling and exploiting the catheter shaft or guide wire. Finally, it is seen that the same cooperation allows the use of what was originally the proximal end zone of the catheter shaft or guide wire to treat the occlusion or to guide other treatment devices.

After the operation, the suction cups 174 may be released, the apparatus withdrawn from the patient, and the incision closed. Importantly, the micro-invasive locator 160 provides the necessary spatial information for guidance of the working element 102 while completely avoiding the gross trauma that would be inflicted upon in the patient by a traditional bypass operation.

Referring again to FIG. 3, an exemplary embodiment of the present invention is shown including the above-described locator 160, catheter shaft 100, lumen 114, steering member 122, and tissue-penetrating wire 116. A metal nose cone 134 is included in the distal end 112 of the catheter shaft 100 and defines a distal opening through which the tissue-penetrating wire 116 can project from the lumen 114. As the tissue-penetrating wire 116 is urged through tissues, the catheter shaft 100 can be steered via the steering member 122 and urged into the tissues along the path made by the wire 116. As the catheter shaft 100 follows the wire 116 through the tissues, the nose cone 134 reduces the resistance encountered by the catheter shaft 100. Progress is observed via the locator 160.

Referring back to FIG. 2 and now particularly to FIG. 7, an exemplary embodiment of the present invention is shown including the above-described locator 160, catheter shaft 100, lumen 114, steering member 122, and tissue-penetrating wire 116 (other work elements may be used, as will be described below). The distal end zone 104 of the catheter shaft 100 also includes a plurality of rings 140. The rings 140 define paths 141 for the steering wires 124 (described above) of the steering member 122. One or more of the rings 140 may serve to anchor the distal ends 128 of the steering wires 124. The distal end zone 104 of the catheter shaft 100 also includes a plurality of slots 142 inscribed therein for increasing the steerability of the distal end zone 104.

Figure 7:
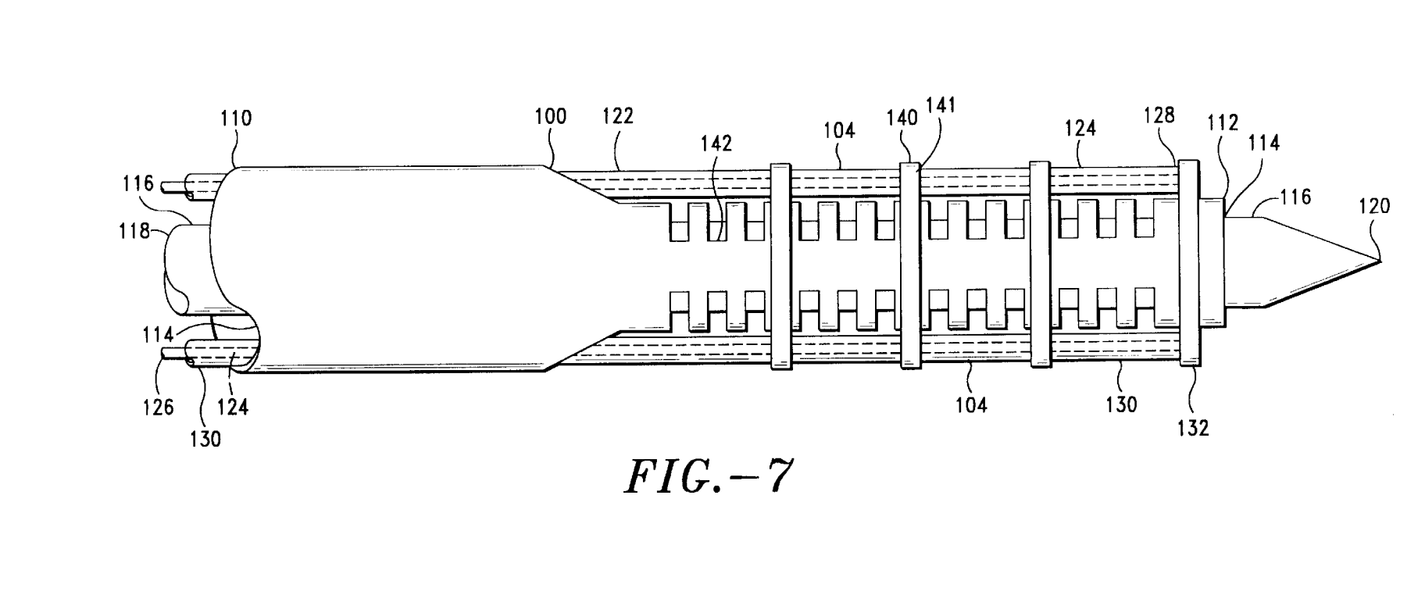
FIG. 7 is an enlarged side view of an exemplary embodiment of an apparatus according to the present invention showing the structure of a catheter shaft including rings and slots in the distal end zone of the catheter shaft.

Continuing with reference to FIG. 7, unequal tension on the steering wires 124 will deflect the distal end zone 104 and the working element 102 toward a wire having greater tension. The slots 142 in the distal end zone 104 of the catheter shaft 100 reduce the force required to compress one side of the distal end zone 104 and extend the opposite side. A steering wire can thus more easily deflect the distal end zone 104. Because the slots 142 only partially circumscribe the distal end zone 104 of the catheter shaft 100, they do not appreciably reduce its axial stiffness. As a result, the distal end 112 of the catheter shaft may still be pushed firmly against a tissue surface at a point where the working element 102 is intended to enter.

Figure 8:
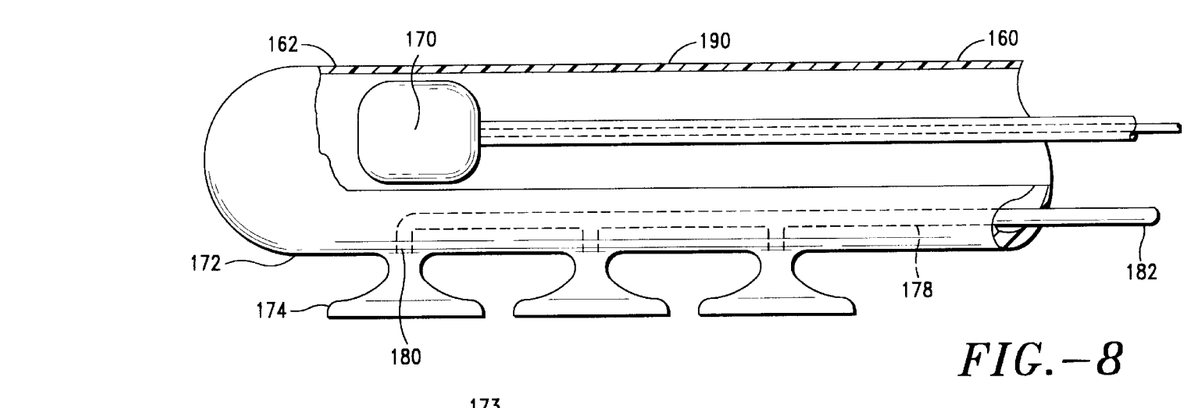
FIG. 8 is an enlarged side view of an exemplary embodiment of an apparatus according to the present invention showing a locator including a plurality of suction coupling surface features.
Figure 9:
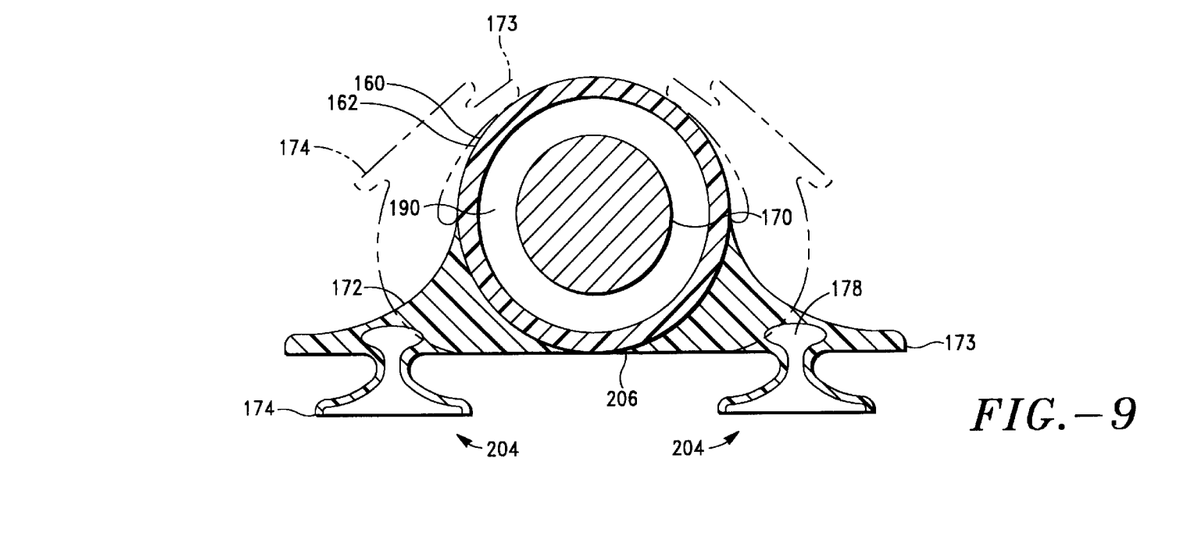
FIG. 9 is an enlarged sectional view of an exemplary embodiment of an apparatus according to the present invention showing a locator including a plurality of suction coupling surface features.

Referring back to FIG. 2 and now particularly to FIGS. 8 and 9, an exemplary embodiment of the present invention is shown in which the imaging tube 162 of the locator 160 includes an exterior surface 172 defining a plurality of suction cups 174. The suction cups 174 are arrayed in two roughly parallel rows 204. Between the rows 204 is a region of the surface defining an imaging window 206. In the exemplary embodiment illustrated in FIG. 8, the imaging window 206 includes an acoustically transparent portion of the imaging tube 162 adjacent the lumen 190. As can be seen in FIG. 8, the transducer 170 has a view through the window 206 unobstructed by the suction cups 174. The imaging tube 162 optionally includes a suction cup activating lumen 178 having a distal end zone 180 communicating with the suction cups 174 and a proximal end 182 coupled with a pressure modulating device (not shown). The lumen 178 and pressure modulating device permit rapid, minimally traumatic temporary stabilization of the imaging tube 162 on the heart surface. Additionally, the catheter delivery lumen 187 terminates proximate the imaging window 206, so that the working element 102 and the distal end zone 104 of the catheter shaft 100 can be observed via the imaging device 168 as they emerge from the lumen 187. In this way, it is possible to shorten the distance the catheter shaft 100 must traverse to reach from the catheter delivery lumen 187 to the artery 60 and thus to the interventionist's control over the catheter shaft 100.

Figure 10:
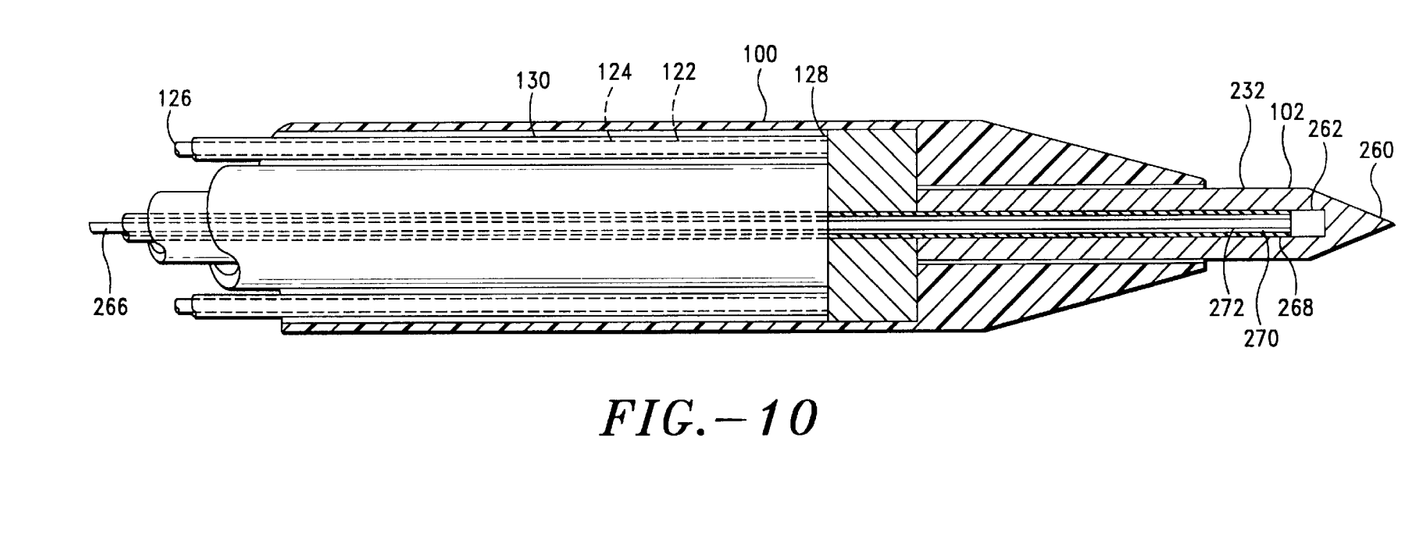
FIG. 10 is an enlarged side view of an exemplary embodiment of an apparatus according to the present invention showing the structure of a catheter shaft including a signal-emitting working element.

Referring back to FIG. 2 and now also to FIG. 10, an exemplary embodiment of the present invention is shown including the above-described locator 160, catheter shaft 100, lumen 114 and steering member 122. In this embodiment, the working element includes a tissue-penetrating working element 102 having a distal end 260. A signal emitter 262 is disposed in the distal end 260. A signal generator (not shown) is operatively coupled to the signal emitter 262. In this embodiment, the signal generator is external to the body and is coupled to the emitter 262 through an electrically conductive path 266 originating in the proximal end zone 106 of the catheter shaft 100 and terminating at the emitter 262. As illustrated, the electrically conductive path 266 includes an outer conductor 268 disposed in the catheter shaft 100, a tubular dielectric layer 270 therein, and an inner conductor 272 disposed within the dielectric layer 270. However, any other energy-delivering or converting means can be employed to energize the emitter 262. When the locator 160 and emitter 262 are activated within the body, the locator 160 selectively detects the signal emitted by the emitter 262 in order to discern a spatial relationship between the working element 102 and the locator 160.

Alternatively, the signal emitter 262 may be disposed in a working element which is essentially a guide wire, optionally steerable. Likewise, the catheter shaft may be of a simpler design than the one shown in FIG. 1 0; in particular, a catheter shaft without a steering member, and a signal-emitting guide wire distal end not surrounded by a separate catheter shaft, are both within the scope of the present invention.

While the foregoing detailed description has described several embodiments of the invention, it is to be understood that the above description is illustrative only and not limiting of the disclosed invention. Particularly, the imaging device need not be an acoustic transducer and need not accomplish its imaging by scanning or mechanical movement in any particular manner. The imaging device may be operatively coupled to external instruments by any appropriate mechanical, electromagnetic, optical, wave guide or other path. The image that is displayed may be computed by any of a variety of algorithms for extracting one-, two-, or three-dimensional information from energy reflected, scattered or absorbed within tissues. The imaging tube may be stabilized proximate the occlusion 62 by any appropriate mechanical, pneumatic, hydraulic or other means. Additionally, the locator 160 need not approach the heart in the particular manner described; alternative routes may be taken.

Likewise, the steering member may include more or fewer than the two wires illustrated in the drawing figures. The working element 102 may include any mechanical, optical, thermal, chemical, or other device for penetrating tissues, treating an occlusion, or delivering a medicament. The catheter shaft 100 and working element 102 may be configured such that only the working element 102 traverses certain tissues or, alternatively, the catheter shaft 100 itself may follow along with the working element 102. It will be appreciated that the embodiments discussed above and the virtually infinite embodiments that are not mentioned could easily be within the scope and spirit of the present invention. Thus, the invention is to be limited only by the claims as set forth below.

What is claimed is:

1. An apparatus for treating arterial occlusions, comprising:
    a locator for extraluminal placement proximate to an arterial occlusion, wherein the locator includes an imaging tube having a proximal end zone, a distal end zone, a lumen therebetween, and an imaging device operatively disposed in the imaging tube; and
    an elongated flexible catheter shaft disposed in the lumen of the imaging tube that is formed with a a distal end zone, wherein the distal end zone of the catheter shaft include a working element that is transvascularly operable upon the occlusion in view of spatial information provided by the locator, and wherein the working element further includes a tissue-penetrating wire at least partially disposed within the working element.

2. The catheter shaft includes a steering member, the steering member including at least one steering wire disposed in the catheter shaft having a distal end zone, wherein the distal end zone of the steering wire has at least one displacing linkage to the distal end zone of the catheter shaft, and the working element has at least one deflecting linkage to the catheter shaft, wherein displacement of the steering wire deflects the distal end zone of the catheter shaft thereby deflecting the working element to direct the working element in a preferred direction.

3. An apparatus as set forth in claim 2, wherein at least one tube is disposed about the steering wire, and wherein the steering wire is slidably positioned with the catheter shaft.

4. An apparatus as set forth in claim 2, wherein a ring is disposed in the distal end zone of the catheter shaft and the steering wire is affixed to the ring, and wherein the distal end of the steering wire is securely anchored in the distal end zone of the catheter shaft.

5. An apparatus as set forth in claim 1, wherein:
the catheter shaft includes a steering member, the steering member including at least one steering wire disposed in the catheter shaft having a distal end zone, wherein the distal end zone of the steering wire having at least one displacing linkage to the working element and displacement of steering wire deflects the working clement to direct the working element in a preferred direction.

6. An apparatus as set forth in claim 1, wherein the tissue-penetrating wire includes a sharpened distal end and is slidably disposed in the catheter shaft, and wherein the distal end of the tissue-penetrating wire is configured for distal advancement relative to the distal end portion of the shaft.

7. An apparatus as set forth in claim 1, wherein the distal end of the working element includes a trocar tip.

8. An apparatus as set forth in claim 1, wherein the working element includes a guide wire.

9. An apparatus as set forth in claim 8, wherein the guide wire is steerable.

10. An apparatus as set forth in claim 8, wherein the guide wire includes a transducer that emits a signal, and wherein the locator detects the signal emitted by the guide wire transducer to provide an anatomical location and orientation of the guide wire while the guide wire is manipulated.

11. An apparatus as set forth in claim 10, wherein the guide wire is steerable.

12. An apparatus as set forth in claim 1 wherein the distal end zone of the catheter shaft includes an outer surface formed with a plurality of slots partially circumscribing the catheter shaft to provide a flexible distal end zone of the catheter shaft without substantial increased axial compressibility.

13. An apparatus as set forth in claim 12, wherein the catheter shaft has a longitudinal axis and the longitudinal axis is circumscribed by a plurality of rings disposed the distal end zone of the catheter shaft, the rings defining a path for a steering wire.

14. An apparatus as set forth in claim 1 wherein the imaging device includes at least one energy transducer and the locator includes a signal generator-processor a operatively coupled to the energy transducer.

15. An apparatus as set forth in claim 14, wherein the imaging tube includes a proximal end zone an a lumen, and further comprising:
a transducer control shaft disposed in the lumen of the imaging tube, wherein the transducer control shaft includes a proximal end zone and a signal conducting path, the signal conducting path being operatively coupled to the signal generator-processor via the proximal end zone; and wherein the locator includes a control shaft driver operatively coupled to the proximal end zone of the transducer control shaft; and the at least one transducer is movably disposed in the lumen, manipulably attached to the transducer control shaft, and operatively coupled to the signal conducting path, and wherein the transducer control shaft driver and the signal generator-processor cooperate with the transducer control shaft and the transducer to provide a scanning image.

16. An apparatus as set forth in claim 15, wherein the transducer control shaft is rotatably disposed in the imaging tube lumen and rotationally driven by the transducer driver.

17. An apparatus as set forth in claim 14, wherein the locator includes at least one acoustic transducer, an acoustic signal generator-processor, and at least one signal conducting path for coupling the transducer to the generator-processor, wherein the working element is operated while the locator provides an acoustically-derived data output embodying the anatomical location and orientation of the working element.

18. An apparatus as set forth in claim 14, wherein the locator acquires and displays an image of the occlusion and of the working element.

19. An apparatus as set forth in claim 14 wherein the signal generator-processor correlates reflected acoustical energy with manipulations of the transducer by the driver, wherein the transducer is physically manipulated within the imaging tube while the signal generator-processor generates an output signal embodying spatially organized data about objects proximate the working element.

20. An apparatus as set forth in claim 14 wherein the transducer is rotatable and translatable by the transducer control shaft driver via the transducer control shaft, and wherein the transducer, driver, and signal generator-processor cooperate to scanningly emit and receive acoustic energy and to generate an output signal embodying the anatomical location and orientation of the working element while the working element is operated.

21. An apparatus as set forth in claim 14 wherein the transducer includes a plurality of acoustic transducers, and wherein the transducers and signal generator-processor cooperate to emit and receive acoustic energy and to generate an output signal embodying the anatomical location and orientation of the working element while the working element is operated.

22. An apparatus as set forth in claim 15, wherein a portion of the imaging tube is flexible.

23. An apparatus as set forth in claim 1, wherein the locator includes means for stabilizing the locator with respect to a surface located within a body.

24. An apparatus as set forth in claim 1, wherein the imaging tube has an exterior surface defining at least one suction coupling area to provide removable adherence to bodily tissues which stabilize positioning of the locator.

25. An apparatus as set forth in cliam 1, wherein the exterior surface of the imaging tube defines an imaging window and a plurality of suction coupling areas disposed peripherally about the window.

26. An apparatus as set forth in claim 24, wherein the locator includes means for selectively activating the suction coupling area.

27. An apparatus as set forth in claim 26, wherein the locator includes a pressure modulating device and at least one pressure communicating path coupling a suction coupling area to the pressure modulating device that selectively activates the suction coupling area.

28. An apparatus as set forth in claim 1 wherein the working element emits a signal and the locator detects the signal emitted by the working element, and wherein anatomical location and orientation of the working element is provided while the working element is operating.

29. An apparatus as set forth in claim 1 wherein the imaging tube includes a suction lumen, at least one imaging window, and an exterior surface defining at least one suction area including an imaging window, the suction lumen communicating with the suction area.

30. A method for treating an arterial occlusion having a distal boundary and a proximal boundary in a human or animal body, comprising the steps of:

providing an apparatus for treating an arterial occlusion, the apparatus comprising a locator including an imaging tube with a proximal end zone, a distal end zone, a lumen therebetween, and an imaging device operatively disposed in the imaging tube; and an elongated flexible catheter shaft, disposed in the lumen of the imaging tube, including a distal end zone and a working element disposed therein;

introducing tee locator into the chest cavity, placing the distal end zone of the locator proximate the distal boundary of the occlusion, activating the locator to discern the anatomical location and position of the working element;

advancing the catheter shaft into contact with the artery while observing the anatomical location and position of the working element via the locator;

advancing the working element through an arterial wall and into the artery; and advancing the working element retrograde within the artery and into and through the occlusion until the working element exits the occlusion via the proximal boundary of the occlusion; wherein the locator, catheter shaft and working element are positioned proximate the occlusion and the working element is operated to cross the occlusion, while the locator reveals the anatomical location and orientation of the working element to accomplish manipulation of the working element.

31. A method as set forth in claim 30, wherein the working element is steerable and further comprising the steps of:

steering the working element across an occlusion upon activation of the locator so that the locator, catheter shaft and working element are positioned proximate the occlusion; and monitor the anatomical location and orientation of the working element a with the locator to accomplish steering and manipulation of the working element.

32. A method as set forth in claim 30, further comprising the steps of:

providing a second catheter adapted for manipulating the working element of the catheter shaft;

placing the second catheter proximal to the occlusion; and positioning the working element of the catheter shaft into contact with the second catheter upon advancement of the working element retrograde within the artery and into the occlusion, and wherein the catheter shaft is manipulable via the working element thereof while positioned across the occlusion.

33. A method as set forth in claim 30, further comprising the steps of:

providing a second catheter adapted for manipulating the working element of the catheter shaft;

introducing the second catheter into the arterial lumen from an entry point proximal to the occlusion, the second catheter includes a proximal end, a distal end and a lumen therebetween; and passing the working element through the lumen of the second catheter to the proximal end thereof upon advancement of the working element retrograde within the artery and into the occlusion, wherein the catheter shaft is manipulable via the working element thereof through the proximal end of the second catheter.

34. A method as set forth in claim 33, further comprising the steps of:

manipulating the working element via the proximal end of the second catheter upon passage of the working element to the proximal end of the second catheter; and drawing the catheter shaft out of the locator imaging tube lumen until the proximal end of the catheter shaft exits the imaging tube lumen and is positioned proximate the distal boundary of the occlusion, wherein the catheter shaft is introduced into the artery from the locator imaging tube lumen, brought under the control by means of the second catheter, and drawn into a position across the occlusion for therapeutic and guiding functions.

35. A method as set forth in claim 30, wherein the catheter shaft consists of a guide wire and the working element consists of the distal end of the guide wire.

* * * * *